United States Patent [19]

Muller et al.

[11] Patent Number: 5,736,570
[45] Date of Patent: Apr. 7, 1998

[54] IMMUNOTHERAPEUTIC ARYL AMIDES

[75] Inventors: George W. Muller, Bridgewater; Mary Shire, North Plainfield; David I. Stirling, Branchburg, all of N.J.

[73] Assignee: Celgene Corporation, Warren, N.J.

[21] Appl. No.: 729,847

[22] Filed: Oct. 15, 1996

Related U.S. Application Data

[62] Division of Ser. No. 366,618, Dec. 30, 1994.
[51] Int. Cl.$^6$ .................. A61K 31/235; A61K 31/165
[52] U.S. Cl. .................. 514/532; 514/535; 514/617; 514/619; 514/622
[58] Field of Search .................. 514/532, 535, 514/617, 619, 622

[56] References Cited

U.S. PATENT DOCUMENTS 5,463,063  10/1995  Muller .................. 546/201

*Primary Examiner*—Jane Fan
*Attorney, Agent, or Firm*—Mathews, Collins, Shepherd & Gould

[57] ABSTRACT

Novel aryl amides are inhibitors of tumor necrosis factor α and can be used to combat cachexia, endotoxic shock, and retrovirus replication. A typical embodiment is N-benzoyl-3-amino-3-(3',4'-dimethoxyphenyl)propanamide.

12 Claims, No Drawings

1

IMMUNOTHERAPEUTIC ARYL AMIDES

This application is a division of application Ser. No. 08/366,618, filed Dec. 30, 1994, (08/366,618 pending).

BACKGROUND OF THE INVENTION

The present invention relates a method of reducing levels of TNFα in a mammal and to compounds and compositions useful therein.

TNFα, or tumor necrosis factor α, is a cytokine which is released primarily by mononuclear phagocytes in response to various immunostimulators. When administered to animals or humans it causes inflammation, fever, cardiovascular effects, hemorrhage, coagulation and acute phase responses similar to those seen during acute infections and shock states.

Excessive or unregulated TNFα production has been implicated in a number of disease conditions. These include endotoxemia and/or toxic shock syndrome {Tracey et al., Nature 330, 662–664 (1987) and Hinshaw et al., Circ. Shock 30, 279–292 (1990)}; cachexia {Dezube et al., Lancet, 335 (8690), 662 (1990)}; and Adult Respiratory Distress Syndrome where TNFα concentration in excess of 12,000 pg/milliliters have been detected in pulmonary aspirates from ARDS patients {Millar et al., Lancet 2 (8665), 712–714 (1989)}. Systemic infusion of recombinant TNFα also resulted in changes typically seen in ARDS {Ferrai-Baliviera et al., Arch. Surg. 124 (12), 1400–1405 (1989)}.

TNFα appears to be involved in bone resorption diseases, including arthritis where it has been determined that when activated, leukocytes will produce a bone-resorbing activity, and data suggest that TNFα contributes to this activity. {Bertolini et al. Nature 319, 516–518 (1986) and Johnson et al., Endocrinology 124 (3), 1424–1427 (1989).} It has been determined that TNFα stimulates bone resorption and inhibits bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46 (Suppl.), S3–10 (1990)}. In Graft versus Host Reaction, increased serum TNFα levels have been associated with major complication following acute allogenic bone marrow transplants {Holler et al., Blood, 75 (4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J. Med. 320 (24), 1586–1591 (1989)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et a., Nature, 344: 245–247 (1990)}. High levels of TNFα production (in the serum and in isolated macrophages) have been demonstrated in animal models of silica and asbestos induced fibrosis {Bissonnette et al., Inflammation 13 (3), 329–339 (1989)}. Alveolar macrophages from pulmonary sarcoidosis patients have also been found to spontaneously release massive quantities of TNFα as compared with macrophages from normal donors {Baughman et al., J. Lab. Clin. Med. 115 (1), 36–42 (1990)}.

TNFα is also implicated in the inflammatory response which follows reperfusion, called reperfusion injury, and is a major cause of tissue damage after loss of blood flow {Vedder et al., PNAS 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J. Path. 135 (1), 121–132 (1989)}.

Moreover, it now is known that TNFα is a potent activator of retrovirus replication including activation of HIV-1. {Duh et al., Proc. Nat. Acad. Sci. 86, 5974–5978 (1989); Poll et al., Proc. Nat. Acad. Sci 87, 782–785 (1990); Monto et al., Blood 79, 2670 (1990); Clouse et al., J. Immunol. 142, 431–438 (1989); Poll et al., AIDS Res. Hum. Retrovirus, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual aids in limiting the maintenance of T lymphocyte caused by HIV infection.

Monocytes, macrophages, and related cells, such as kupffer and glial cells, have also been implicated in maintenance of the HIV infection. These cells, like T cells, are targets for viral replication and the level of viral replication is dependent upon the activation state of the cells. {Rosenberg et al., The Immunopathogenesis of HIV Infection, Advances in Immunology, 57 (1989)}. Cytokines, such as TNFα, have been shown to activate HIV replication in monocytes and/or macrophages {Poli et al. Proc. Natl. Acad. Sci, 87, 782–784 (1990)}, therefore, prevention or inhibition of cytokine production or activity aids in limiting HIV progression as stated above for T cells. Additional studies have identified TNFα as a common factor in the activation of HIV in vitro and has provided a clear mechanism of action via a nuclear regulatory protein found in the cytoplasm of cells (Osborn, et al., PNAS 86, 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS associated cachexia is suggested by elevated serum TNFα and high levels of spontaneous TNFα production in peripheral blood monocytes from patients {Wright et al. *J. Immunol.* 141 (1), 99–104 (1988)}.

TNFα has been implicated in various roles with other viral infections, such as the cytomegalia virus (CMV), influenza virus, adenovirus, and the herpes family of viruses for similar reasons as those noted.

Preventing or inhibiting the production or action of TNFα is, therefore, predicted to be a potent therapeutic strategy for many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Efforts directed to the suppression of the effects of TNFα have ranged from the utilization of steroids such as dexamethasone and prednisolone to the use of both polyclonal and monoclonal antibodies {Beutler et al., *Science* 234, 470–474 (1985); WO 92/11383}.

The nuclear factor κB (NFκB) is a pleiotropic transcriptional activator (Lenardo, et al. *Cell* 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al. *J. Biol. Chem.* 1993, 17762–66; Duh et al. *Proc. Natl. Acad. Sci.* 1989, 86, 5974–78; Bachelerie et al. *Nature* 1991, 350, 709–12; Boswas et al. *J., Acquired Immune Deficiency Syndrome* 1993, 6, 778–786; Suzuki et al. *Biochem. And Biophys. Res. Comm.* 1993, 193, 277–83; Suzuki et al *Biochem. And Biophys. Res Comm.* 1992, 189, 1709–15; Suzuki et al. *Biochem. Mol. Bio. Int.* 1993, 31 (4), 693–700; Shakhov et al. 1990, 171, 35–47; and Staal et al. *Proc. Natl. Acad. Sci. USA* 1990, 87, 9943–47). Thus, inhibition of NFκB binding can regulate transcription of cytokine gene(s) and through this modulation and other mechanisms be useful in the inhibition of a multitude of disease states. The compounds claimed in this patent can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS.

TNFα and NFκB levels are influenced by a reciprocal feedback loop. As noted above, the compounds of the present invention affect the levels of both TNFα and NFκB. It is not known at this time, however, how the compounds of the present invention regulate the levels of TNFα, NFκB, or both.

DETAILED DESCRIPTION

The present invention is based on the discovery that a class of non-polypeptide imides more fully described herein appear to inhibit the action of TNFα.

The present invention pertains to compounds of the formula:

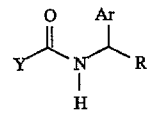

in which

Ar is (i) straight, branched, or cyclic, unsubstituted alkyl of 1 to 12 carbon atoms; (ii) straight, branched, or cyclic, substituted alkyl of 1 to 12 carbon atoms; (iii) phenyl; (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or halo; (v) heterocycle; or (vi) heterocycle substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo;

R is —H, alkyl of 1 to 10 carbon atoms, $CH_2OH$, $CH_2CH_2OH$, or $CH_2COZ$ where Z is alkoxy of 1 to 10 carbon atoms, benzyloxy, or $NHR^1$ where $R^1$ is H or alkyl of 1 to 10 carbon atoms; and, Y is i) a phenyl or heterocyclic ring, unsubstituted or substituted one or more substituents each selected independently one from the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo or ii) naphthyl.

A first preferred subclass pertains to compounds in which Ar is phenyl substituted with two methoxy groups;

R is $CH_2CO_2CH_3$; and

Y is a phenyl ring, unsubstituted or substituted with one amino group.

Typical compounds of this invention include:

3-(N-benzoylamino)-3-(3,4-dimethoxyphenyl) propionamide, 3-(N-benzoylamino)-3-(3,4-diethoxyphenyl) propionamide, 3-(N-benzoylamino)-3-(3,4-diethylphenyl)propionamide, 3-(N-benzoylamino)-3-cyclohexylpropionamide, 3-[N-(3-aminobenzoyl)amino]-3-(3,4-diethoxyphenyl) propionamide, 3-[N-(3-methoxybenzoyl)amino]-3-(3,4-diethoxyphenyl) propionamide, 3-[N-(4-methoxybenzoyl)amino]-3-(3,4-diethoxyphenyl) propionamide, methyl 3-(N-benzoylamino)-3-(3,4-diethoxypenyl) propionate, methyl 3-[N-(3-aminobenzoyl)amino]-3-(3,4-diethoxyphenyl)propionate, methyl 3-[N-(3-methoxybenzoyl)amino]-3-(3,4-diethoxyphenyl)propionate, methyl 3-[N-(4-methoxybenzoyl)amino]-3-(3,4-diethoxyphenyl)propionate.

methyl 3-(N-benzoylamino)-3-(4-trifluoromethylphenyl)propionate.

methyl 3-(N-benzoylamino)-3-(4-acetylphenyl)propionate.

The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain from 1 to 6 carbon atoms. The same carbon content applies to the parent term "alkane" and to derivative terms such as "alkoxy".

The compounds can be used, under the supervision of qualified professionals, to inhibit the undesirable effects of TNFα. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 500 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is soon following the normal treatment regimen, then the amount of cytokine activity interfering agent administered is increased, e.g., by fifty percent a week.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Certain of these compounds possess centers of chirality and can exist as optical isomers. Both the racemates of these isomers and the individual isomers themselves, as well as diastereoisomers when there are two chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid, such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

Prevention or inhibition of production of TNFα by these compounds can be conveniently assayed using anti-TNFα antibodies. For example, plates (Nunc Immunoplates, Roskilde, DK) are treated with 5 μg/milliliter of purified rabbit anti-TNFα antibodies at 4° C. for 12 to 14 hours. The plates then are blocked for 2 hours at 25° C. with PBS/0.05% Tween containing 5 milligrams/milliliter BSA. After washing, 100 μL of unknowns as well as controls are applied and the plates incubated at 4° C. for 12 to 14 hours. The plates are washed and assayed with a conjugate of peroxidase (horseradish) and mouse anti-TNFα monoclonal antibodies, and the color developed with o-phenylenediamine in phosphate-citrate buffer containing 0.012% hydrogen peroxide and read at 492 nm.

The compounds can be prepared using methods which are known in general for the preparation of imides. General reaction schemes include the reaction of the substituted amine or ammonium with substituted benzoyl chloride as illustrated by the formulas:

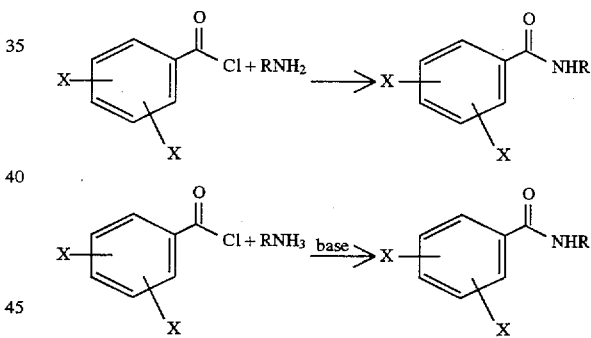

The following examples will serve to further typify the nature of this invention but should not be construed as a limitation in the scope thereof, which scope is defined solely by the appended claims.

EXAMPLE 1

Methyl N-benzoyl-3-amino-3-(3,4-dimethoxyphenyl)propionate. To an ice bath cooled stirred suspension of methyl 3-amino-3-(3,4-dimethoxyphenyl)propionate hydrochloride (0.689 grams, 2.50 mmol) and triethylamine (0.7 milliliters, 5 mmol) in 15 milliliters of tetrahydrofuran was added 0.3 milliliters of benzoyl chloride (2.6 mmol). The cooling bath was removed after 15 minutes and the mixture stirred for an additional 45 minutes. The reaction mixture was then diluted with 15 milliliters of brine and 15 milliliters of water and then partially concentrated in vacuo to remove the tetrahydrofuran. The reaction slurry was filtered, the solid air-dried, then dried in vacuo (60° C., <1 mm) to afford 0.86 g (100%) of the product as a white powder: $^1$H NMR (dmso-d$_6$, 250 MHz) δ 8.84 (d, J=8.3 Hz, 1 H, NH), 7.83 (m, 2 H, Ar), 7.60–7.35 (m, 3 H, Ar), 7.06 (s, 1 H, Ar), 6.90 (m, 2 H, Ar), 5.50–5.30 (m, 1 H, CHN), 3.75 (s, 3 H, OCH$_3$), 3.72 (s, 3 H, OCH$_3$), 3.46 (s, 3 H, CO$_2$CH$_3$), 3.05–2.75 (m, 2 H, CH$_2$); $^{13}$C NMR (dmso-d$_6$) δ 170.8, 165.6, 148.6, 147.9, 134.9, 134.5, 131.2, 128.3, 127.3, 118.5, 111.6, 110.6, 55.5, 55.5, 51.4, 49.7, 40.6. Anal. Calcd for C$_{19}$H$_{21}$NO$_5$. Theoretical C, 66.46; H, 6.16; N, 4.08. Found C, 66.22; H, 6.05; N, 3.98.

EXAMPLE 2

Methyl N-(3-nitrobenzoyl)-3-amino-3-(3,4-dimethoxyphenyl)propionate. To an ice bath cooled stirred suspension of methyl 3-amino-3-(3,4-dimethoxyphenyl) propionate hydrochloride (1.38 grams, 5.00 mmol) and triethylamine (1.5 milliliters, 10.8 mmol) in 10 milliliters of tetrahydrofuran was added 3-nitrobenzoyl chloride (0.928 grams, 5.00 mmol) in a single portion. A thick slurry resulted. The cooling bath was removed after 15 minutes, the mixture diluted with 10 milliliters of tetrahydrofuran and the mixture stirred for an additional hour. The reaction mixture was diluted with 50 milliliters of water and then partially concentrated in vacuo to remove the tetrahydrofuran. The reaction slurry was filtered, the solid washed with copious amounts of water, air-dried, and dried in vacuo (60° C., <1 mm) to afford 1.85 grams (95%) of the product as an off white powder: $^1$H NMR (CDCl$_3$, 250 MHz) δ 8.63 (t, J=1.9 Hz, 1 H), 8.35 (m, 1 H, Ar), 8.20 (m, 1 H, Ar), 7.77 (d, J=8 Hz, 1 H, NH), 7.63 (t, J=8.0 Hz, 1 H), 6.95–6.75 (m, 3 H, Ar), 5.86 (m, 1 H, CHCO), 3.85 (s, 3 H, OCH$_3$), 3.84 (s, 3 H, OCH$_3$), 3.68, (s, 3 H, CO$_2$CH$_3$), 3.01 (m, 2 H, CH$_2$); $^{13}$C NMR (CDCl$_3$) δ 172.0, 164.1, 149.1, 148.6, 148.2, 135.8, 133.1, 132.7, 129.8, 126.1, 122.0, 118.2, 111.2, 109.9, 55.9, 55.8, 52.0, 50.2, 39.5.

EXAMPLE 3

Methyl N-(3-aminobenzoyl)-3-amino-3-(3,4-dimethoxyphenyl) propionate. To a solution of methyl N-(3-nitrobenzoyl)-3-amino-3-(3,4-dimethoxyphenyl)propionate (1.25 grams, 3.22 mmol) in a mixture of 150 milliliters of ethyl acetate and 75 milliliters of methanol (mixture gently warmed to dissolve all solid and then allowed to cool to room temperature) was added 0.25 grams of 10% Pd/C. The mixture was then treated with 60 psi of H$_2$ for 2.5 hours on a Parr Type Shaker. Reaction progress was monitored by TLC (1/9 ethyl acetate/methylene chloride, UV) and was complete after 2.5 hours. The reaction mixture was filtered through celite to remove catalyst. The filtrate was concentrated in vacuo to afford a white solid which was dried in vacuo (60° C., <1 mm) to afford 1.07 grams (93%) of the desired product: $^1$H NMR (dmso-d$_6$, 250 MHz) δ 8.60 (d, J=8.5 Hz, 1 H, NH), 7.15–6.8 (m, 6 H, Ar), 6.67 (m, 1 H, Ar), 5.40 (m, 1 H, CHCO), 5.24 (m 2 H, ArNH$_2$), 3.75 (s, 3 H, OCH$_3$), 3.72 (s, 3 H, OCH$_3$), 3.56 (s, 3 H, CO$_2$CH$_3$), 2.95 (dd, J=8.9, 15.4 Hz, 1 H), 2.81 (dd, J=6.3, 15.4 Hz, 1 H); $^{13}$C NMR (dmso-d$_6$) δ 170.9, 166.4, 148.6, 148.6, 147.8, 135.6, 135.1, 128.6, 118.5, 116.4, 114.4, 112.8, 111.6, 110.6, 55.5, 55.5, 51.4, 49.6, 40.7.

EXAMPLE 4

Methyl N-(4-nitrobenzoyl)-3-amino-3-(3,4-dimethoxyphenyl)propionate. To an ice bath cooled stirred suspension of methyl 3-amino-3-(3,4-dimethoxyphenyl) propionate hydrochloride(1.38 grams, 5.00 mmol) and triethylamine (1.5 milliliters, 10.8 mmol) in 25 milliliters of tetrahydrofuran was added 4-nitrobenzoyl chloride (0.928 grams, 5.00 mmol) in a single portion. After 15 minutes, the cooling bath was removed and the reaction mixture stirred for 45 minutes. The reaction mixture was then diluted with 50 milliliters of water. The reaction slurry was filtered and the solid washed with water, air-dried, and then dried in vacuo (60 C., <1 mm) to afford 1.86 grams (94%) of the product as a yellow powder: $^1$H NMR (CDCl$_3$/TMS, 250 MHz) δ 8.27 (d, J=8.8 Hz, 2 H), 7.98 (d, J=8.8 Hz, 2 H), 7.77 (d, J=8.1 Hz, 1 H, NH), 6.95–6.75 (m, 3 H, Ar), 5.55 (m, 1 H, CH), 3.86 & 3.85 (2 s, 6 H, 2 OCH$_3$), 3.68 (s, 3 H, CO$_2$CH$_3$), 3.00 (m, 2 H, CH$_2$); $^{13}$C NMR (CDCl$_3$/TMS) δ 172.2, 164.4, 149.6, 1491, 148.7, 139.7, 132.6, 128.2, 123.8, 118.1, 111.2, 109.9, 55.9, 55.8, 52.0, 50.0, 39.3.

EXAMPLE 5

Methyl N-(4-aminobenzoyl)-3-amino-3-(3,4-dimethoxyphenyl)propionate. To a solution of methyl N-(3-nitrobenzoyl)-3-amino-3-(3,4-dimethoxyphenyl)propionate (1.25 grams, 3.22 mmol) in a mixture of 100 milliliters of ethyl acetate and 50 milliliters of methanol (mixture gently warmed to dissolve all solid and then allowed to cool to room temperature) was added 0.25 grams of 10% Pd/C. The mixture was then treated with 60 psi of H$_2$ for 2.5 hours on a Parr Type Shaker. Reaction progress was monitored by TLC (1/9 ethyl acetate/methylene chloride, UV) and was complete after 2.5 hours. The reaction mixture was filtered through celite to remove catalyst. The filtrate was concentrated in vacuo to afford a white solid which was dried in vacuo (60° C., <1 mm) to afford 1.10 grams (96%) of the desired product: $^1$H NMR (dmso-d$_6$, 250 MHz) δ 8.32 (d, J=8.5 Hz, 1 H, NH), 7.57 (d, J=8.6 Hz, 1 H, Ar), 7.03 (s, 1 H, Ar), 6.88 (m, 2 H, Ar), 6.54 (d, J=8.6, 2 H, Ar), 5.62 (s, 2 H, NH$_2$), 5.38 (m, 1 H, CHCO$_2$), 3.74 (s, 3 H, OCH$_3$), 3.71 (s, 3 H, OCH$_3$), 3.56 (s, 3 H, CO$_2$CH$_3$), 2.94 (dd, J=8.8, 15.3 Hz, 1 H), 2.80 (dd, J=6.5, 15.3, 1 H); $^{13}$C NMR (dmso-d$_6$) δ 170.9, 165.5, 151.7, 148.5, 147.8, 135.4, 128.8, 121.1, 118.5, 112.5, 111.6, 110.6, 55.5, 55.5, 51.3, 49.4, 40.8.

EXAMPLE 6

Methyl N-(3-methoxybenzoyl)-3-amino-3-(3',4'-dimethoxyphenyl)propionate. To an ice bath stirred suspension of methyl 3-amino-3-(3',4'-dimethoxyphenyl) propionate hydrochloride (0.689 grams, 2.50 mmol) and 0.7 milliliters of triethylamine in 20 milliliters of anhydrous tetrahydrofuran was added 3-methoxybenzoyl chloride (2.5 mmol) via syringe. After 30 minutes, the reaction mixture was allowed to warm to room temperature and stirred for 1 hour. The reaction mixture was then treated with 20 milliliters of water. The tetrahydrofuran was removed in vacuo and the resulting mixture extracted with methylene chloride (2 times with 25 milliliters). The combined extracts were dried over sodium sulfate and contracted to afford a thick oil. The crude product was purified by flash chromatography (silica gel, 1.4/8.6 ethyl acetate/hexanes) to afford 0.5 grams (56%) as a pale green solid (wax): mp 123.5°–125° C.; $^1$H NMR (CDCl$_3$/TMS) δ 8.96 (d, J=7.9, 1 H), 8.19 (m, 1 H), 7.45 (m, 1 H), 7.12–6.68 (m, 5 H), 5.59 (m, 1 H), 4.00 (s, 3 H, OCH$_3$), 3.87 (s, 3 H, OCH$_3$), 3.85 (s, 3 H, OCH$_3$), 3.63 (s, 3 H, OCH$_3$), 2.96 (m, 2 H, CH$_2$); $^{13}$C NMR (CDCl$_3$/TMS) δ 171.6, 164.4, 157.6, 148.9, 148.2, 133.8, 132.8, 132.3, 121.3, 121.2, 118.1, 111.3, 111.2, 109.9, 55.8, 55.8, 51.6, 49.7, 40.4; TLC (2/8 ehtyl acetate/hexanes, UV) R$_f$=0.26. Anal. Calcd for C$_{20}$H$_{23}$NO$_6$. Theory C, 64.33; H, 6.21; N, 3.75. Found C, 64.31; H, 6.25; N, 3.63.

EXAMPLE 7

Methyl N-nicotinoyl-3-amino-3-(3',4'-dimethoxyphenyl) propionate. To a cooled (0° C.) stirred suspension of 3-amino-3-(3',4'-dimethoxyphenyl)propionate hydrochloride (1.38 grams, 5.0 mmol) and triethylamine (1.5 milliliters, 10.8 mmol) in 20 milliliters of tetrahydrofuran was added nicotinoyl chloride hydrochloride (0.89 grams, 5.0 mmol). The thick slurry was stirred for 15 minutes and then allowed to warm to room temperature and stirring was continued for 2 hours. The reaction mixture was treated with 20 milliliters of water resulting in a brown colored solution. The tetrahydrofuran was removed in vacuo and the aqueous layer was extracted with methylene chloride (3 times, 25 milliliters). The combined extracts were dried over magnesium sulfate and concentrated in vacuo to afford an oil which solidified overnight. The white solid was dried in vacuo (60° C., <1 mm) to afford 0.52 grams (30%) of crude product. The crude product was purified by flash chromatography (silica gel, 5% methanol/methylene chloride) and dried in vacuo (60° C., <1 mm) to afford 0.38 grams (22%) of the product as a white solid: $^1$H NMR (CDCl$_3$) δ 9.10–9.00(m, 1 H), 8.80–8.69(m, 1 H), 8.19–8.08(m, 1 H), 7.65–7.31(m, 2 H), 6.96–6.76(m, 3 H), 5.64–5.50(m, 1 H), 3.87(s, 3 H), 3.86(s, 3 H), 3.67(s , 3 H), 3.14–2.37(m , 2 H). $^{13}$C NMR (CDCl$_3$) δ 172.1, 164.6, 152.4, 149.2, 148.7, 148.1, 135.0, 132.8, 129.9, 123.5, 118.1, 111.3, 111.2, 109.9, 109.8, 55.9, 52.0, 49.8, 39.5. HPLC 99.47%.

EXAMPLE 8

Methyl N-acetyl-3-(3,4-dimethoxyphenyl)propionate. To an ice bath cooled stirred suspension of methyl 3-amino-3-(3,4-dimethoxyphenyl)propionate hydrochloride (1.97 grams, 7.14 mmol) and triethylamine (2.15 milliliters, 15.43 mmol) in 30 milliliters of tetrahydrofuran was added acetyl chloride (0.51 milliliters, 7.14 mmol). The cooling bath was removed after 15 minutes and the mixture stirred for an additional 2 hours. The reaction mixture was diluted with water (25 milliliters) and was then partially concentrated in vacuo to remove the tetrahydrofuran. The remaining aqueous mixture was extracted with methylene chloride (3 times, 20 milliliters) and the combined organic extracts were dried over magnesium sulfate. The methylene chloride was removed in vacuo to afford 1.40 grams of crude product as an orange oil. The crude product was purified by flash chromatography (silica gel, 5% methanol/methylene chloride) to afford 1.22 grams of product as an oil which later solidified, some minor impurities persisted and the solid was recrystallized from hexane/ethyl acetate. The white solid was dried in vacuo (60° C., <1 mm) to afford 0.81 grams (41%) of product as a white solid: $^1$H NMR (CDCl$_3$) δ 6.92–6.79(m, 3 H), 6.56–6.39(m, 1 H), 5.45–5.03 (m, 1 H), 3.87(s, 3 H), 3.86(s, 3 H), 3.63(s, 3 H), 3.02–2.75 (m, 2 H), 2.02(s, 3 H); $^{13}$C NMR (CDCl$_3$) δ 171.7, 169.2, 149.1, 148.5, 133.1, 118.1, 111.2, 110.0, 55.9, 51.8, 49.4, 39.7, 23.4; HPLC 98.63%.

EXAMPLE 9

Tablets, each containing 50 milligrams of active ingredient, can be prepared in the following manner:

| Constituents (for 1000 tablets) | |
| --- | --- |
| active ingredient | 50.0 grams |
| lactose | 50.7 grams |
| wheat starch | 7.5 grams |
| polyethylene glycol 6000 | 5.0 grams |
| talc | 5.0 grams |
| magnesium stearate | 1.8 grams |
| demineralized water | q.s. |

The solid ingredients are first forced through a sieve of 0.6 mm mesh width. The active ingredient, the lactose, the talc, the magnesium stearate and half of the starch then are mixed. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 10

Tablets, each containing 100 milligrams of active ingredient, can be prepared in the following manner:

| Constituents (for 1000 tablets) | |
| --- | --- |
| active ingredient | 100.0 grams |
| lactose | 100.0 grams |
| wheat starch | 47.0 grams |
| magnesium stearate | 3.0 grams |

All the solid ingredients are first forced through a sieve of 0.6 mm mesh width. The active ingredient, the lactose, the magnesium stearate and half of the starch then are mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 11

Tablets for chewing, each containing 75 milligrams of active ingredient, can be prepared in the following manner:

| Composition (for 1000 tablets) | |
| --- | --- |
| active ingredient | 75.0 grams |
| mannitol | 230.0 grams |
| lactose | 150.0 grams |
| talc | 21.0 grams |
| glycine | 12.5 grams |
| stearic acid | 10.0 grams |
| saccharin | 1.5 grams |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 12

Tablets, each containing 10 milligrams of active ingredient, can be prepared in the following manner:

| Composition (for 1000 tablets) | |
|---|---|
| active ingredient | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 13

Gelatin dry-filled capsules, each containing 100 milligrams of active ingredient, can be prepared in the following manner:

| Composition (for 1000 capsules) | |
|---|---|
| active ingredient | 100.0 grams |
| microcrystalline cellulose | 30.0 grams |
| sodium lauryl sulphate | 2.0 grams |
| magnesium stearate | 8.0 grams |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

EXAMPLE 14

A 0.2% injection or infusion solution can be prepared, for example, in the following manner:

| active ingredient | 5.0 grams |
|---|---|
| sodium chloride | 22.5 grams |
| phosphate buffer pH 7.4 | 300.0 grams |
| demineralized water | to 2500.0 milliliters |

The active ingredient is dissolved in 1000 milliliters of water and filtered through a microfilter. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of active ingredient).

What is claimed is:

1. The method of reducing levels of TNFα in a mammal which comprises administering thereto an effect amount of a compound of the formula:

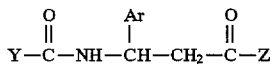

where
- Ar is 3,4-disubstituted phenyl where each substituent is selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;
- Z is alkoxy of 1 to 10 carbon atoms, benzyloxy, amino, or alkylamino of 1 to 10 carbon atoms; and
- Y is (i) a phenyl, unsubstituted or substituted with one or more substituents each selected, independently one from the other, from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, or (ii) naphthyl.

2. The method of claim 1 wherein Ar is phenyl substituted with two methoxy groups.

3. The method of claim 1 wherein Z is $OCH_3$.

4. The method of claim 1 wherein Y is unsubstituted or substituted phenyl and Z is alkoxy, amino, or alkylamino.

5. The method of claim 1 wherein Y is naphthyl.

6. The method according to claim 1 where said compound is selected from the group consisting of 3-(N-benzoylamino)-3-(3,4-dimethoxyphenyl)propionamide, 3-(N-benzoylamino)-3-(3,4-diethoxyphenyl)propionamide, 3-(N-benzoylamino)-3-(3,4-diethylphenyl)propionamide, 3-[N-(3-aminobenzoyl)amino]-3-(3,4-diethoxyphenyl)propionamide, 3-[N-(3-methoxybenzoyl)amino]-3-(3,4-diethoxyphenyl)propionamide, 3-[N-(4-methoxybenzoyl)amino]-3-(3,4-diethoxyphenyl)propionamide, methyl 3-(N-benzoylamino)-3-(3,4-diethoxyphenyl)propionate, methyl 3-[N-(3-aminobenzoyl)amino]-3-(3,4-diethoxyphenyl)propionate, methyl 3-[N-(3-methoxybenzoyl)amino]-3-(3,4-diethoxyphenyl)propionate, and methyl 3-[N-(4-methoxybenzoyl)amino]-3-(3,4-diethoxyphenyl)propionate.

7. The method of inhibiting TNFα-activated retrovirus replication in a mammal which comprises administering thereto an effect amount of a compound of the formula:

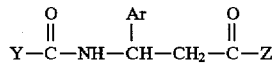

where
- Ar is 3,4-disubstituted phenyl where each substituent is selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;
- Z is alkoxy of 1 to 10 carbon atoms, benzyloxy, amino, or alkylamino of 1 to 10 carbon atoms; and
- Y is (i) a phenyl, unsubstituted or substituted with one or more substituents each selected, independently one from the other, from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, or (ii) naphthyl.

8. The method of claim 7 wherein Ar is phenyl substituted with two methoxy groups.

9. The method of claim 7 wherein Z is $OCH_3$.

10. The method of claim 7 wherein Y is unsubstituted or substituted phenyl and Z is alkoxy, amino, or alkylamino.

11. The method of claim 7 wherein Y is naphthyl.

12. The method according to claim 7 where said compound is selected from the group consisting of 3-(N-benzoylamino)-3-(3,4-dimethoxyphenyl)propionamide, 3-(N-benzoylamino)-3-(3,4-diethoxyphenyl)propionamide, 3-(N-benzoylamino)-3-(3,4-diethylphenyl)propionamide, 3-[N-(3-aminobenzoyl)amino]-3-(3,4-diethoxyphenyl) propionamide, 3-[N-(3-methoxybenzoyl)amino]-3-(3,4-diethoxyphenyl)propionamide, 3-[N-(4-methoxybenzoyl) amino]-3-(3,4-diethoxyphenyl)propionamide, methyl 3-(N-benzoylamino)-3-(3,4-diethoxyphenyl)propionate, methyl 3-[N-(3-aminobenzoyl)amino]-3-(3,4-diethoxyphenyl) propionate, methyl 3-[N-(3-methoxybenzoyl)amino]-3-(3,4-diethoxyphenyl)propionate, and methyl 3-[N-(4-methoxybenzoyl)amino]-3-(3,4-diethoxyphenyl)propionate.

* * * * *